United States Patent [19]
Bos et al.

[11] Patent Number: 5,456,674
[45] Date of Patent: Oct. 10, 1995

[54] CATHETERS WITH VARIABLE PROPERTIES

[75] Inventors: Johannes Bos, Miami Lakes, Fla.; Frans Mous, Drachten; Johannes G. M. van Muiden, Peize, both of Netherlands

[73] Assignee: Cordis Corporation, Miami Lakes, Fla.

[21] Appl. No.: 220,236

[22] Filed: Mar. 30, 1994

[30] Foreign Application Priority Data

Mar. 31, 1993 [NL] Netherlands ............... 9300572

[51] Int. Cl.⁶ .................................. A61M 25/00
[52] U.S. Cl. ........................... 604/280; 604/282
[58] Field of Search ................. 604/280, 282; 138/125, 128, 151, 156, 170, 171

[56] References Cited

U.S. PATENT DOCUMENTS

| | | | |
|---|---|---|---|
| 3,498,286 | 3/1970 | Polanyi et al. | 604/282 |
| 3,752,617 | 8/1973 | Burlis et al. | |
| 3,825,036 | 7/1974 | Stent. | |
| 4,027,659 | 6/1977 | Slingluff | 604/280 |
| 4,182,582 | 1/1980 | Youval et al. | |
| 4,276,250 | 6/1981 | Satchell et al. | |
| 4,402,685 | 9/1983 | Buhler et al. | 604/280 |
| 4,469,483 | 9/1984 | Becker et al. | 604/280 |
| 4,657,024 | 4/1987 | Coneys | 604/280 |
| 4,874,305 | 10/1989 | McGill et al. | |
| 5,176,660 | 1/1993 | Truckai | 604/282 |
| 5,226,899 | 7/1993 | Lee et al. | 604/280 |

FOREIGN PATENT DOCUMENTS

| | | |
|---|---|---|
| 0369383 | 11/1989 | European Pat. Off. . |
| 0385942 | 2/1990 | European Pat. Off. . |
| 4032869 | 10/1990 | European Pat. Off. . |
| 0448886 | 12/1990 | European Pat. Off. . |
| 2191145 | 6/1987 | United Kingdom . |

*Primary Examiner*—C. Fred Rosenbaum
*Assistant Examiner*—Frank Wilkens, III
*Attorney, Agent, or Firm*—Lockwood, Alex, Fritzgibbon & Cummings

[57] ABSTRACT

Catheters manufactured by extrusion are described along with methods and devices for their manufacture. Catheters are manufactured according to the invention by simultaneously conveying a plurality of streams of different materials to a molding nozzle and merging the streams together to form a catheter. An apparatus for the manufacture of such catheters includes means for opening and closing the flow of materials in a controlled manner to thereby vary the composition within the finished extrusion profile. The finished extrusion profile is provided as a catheter containing at least one wall section having bands of different materials extending longitudinally along the length of the catheter.

10 Claims, 2 Drawing Sheets

CATHETERS WITH VARIABLE PROPERTIES

BACKGROUND AND BRIEF DESCRIPTION OF THE INVENTION

The invention relates to catheters with varying physical properties long their length such as varying degrees of rigidity. More specifically, the invention relates to catheters as well as methods and devices for their manufacture wherein the catheters are made with streams of at least two materials which are co-extruded to form a final extrusion profile having a plurality of longitudinally disposed sections of varying composition.

Methods and devices have been proposed for the manufacture of extrusion profiles having variable properties along the length thereof such as varying degrees of rigidity. One such extrusion profile has been proposed having distinct longitudinal sections with each section made of a different material, thereby varying certain properties along the length of the extrusion profile. Another approach is to have circumferentially divided material strips for increasing the stiffness of the tubing. The strips are continuous and extend along the longitudinal axis of the extrusion profile, but are encapsulated by a softer biocompatible base material. In still another approach, blow molding techniques are utilized in the manufacture of a hollow plastic product which varies somewhat in composition, combining two different thermoplastic resin materials to form a single hollow plastic product.

It would be desirable to manufacture an extrusion profile such as a catheter, for example, having areas of differing material compositions and wherein the overall composition of the profile varies along its longitudinal axis, resulting in varying properties at different cross sectional portions of the profile. It would also be desirable to be able to provide the aforementioned profile in the manufacture of catheters for use in angiographic applications, for example. Preferably, these catheters would be pliable or of limited stiffness at the distal end thereof in order to easily follow the course of a blood vessel while being of a more rigid consistency at the proximal end of the catheter to convey pressure exerted on the catheter to its distal end. It would also be advantageous to manufacture catheters, as described herein, using an extrusion device capable of providing streams of molten material wherein certain streams can be easily turned on or off to selectively produce within one length of the extrusion profile a number of sections having somewhat different physical properties.

The present invention overcomes the shortcomings of the prior art by providing certain types of extrusion profiles such as catheters as well as a method and device for their manufacture. In accordance with the invention, catheters are manufactured by an extrusion process whereby streams of molten material are combined to form a single extrusion profile and wherein one or more of the streams can be turned on or off during the process to produce within one length of the extrusion profile a number of sections wherein certain physical properties are altered from one section to the next.

Catheters of the invention are manufactured to include longitudinal bands of different materials. The catheter is manufactured by simultaneously extruding a plurality of divided streams of molten material and conveying the aforementioned streams simultaneously through a molding nozzle where they are joined to form a catheter made of at least two different materials. Each of the streams is conveyed through an extrusion nozzle to feeder lines. At least some of the feeder lines can be turned on and off in a controlled manner to control the longitudinal extent of the individual streams within the finished catheter. The cross sections of one or more of the individual streams can be reduced while the cross section of an adjoining band can be increased correspondingly to vary the physical properties such as the stiffness or rigidity of the catheter.

In this manner, physical characteristics of the catheter catheter can be controlled by including certain selected materials within the wall of the catheter. Stiffer materials, for example, can be incorporated in certain sections of the catheter to provide additional stiffness along a portion of the catheter as desired. Angiographic catheters, for example, can be manufactured to be more pliable or of more limited stiffness at the distal end thereof to thereby permit the catheter to easily follow the course of a blood vessel. The proximal end of such a catheter can be manufactured with stiffer materials to convey pressure to its distal end. Fiber bundles can also be incorporated into the extrusion profile during the extrusion process in order to position materials of greater stiffness within the manufactured catheter.

A device for the manufacture of catheters according to the invention includes at least a pair of extruders each of which supplies a plurality of material strips to a single molding nozzle where the materials converge to form an extrusion profile such as a catheter, for example. Distribution lines from at least one of the extruders are provided with cut off valves to increase or decrease the flow of material forming individual material strips. The two extruders can supply two different materials which are combined through a molding nozzle to form a single extrusion profile. Physical properties such as stiffness can be varied in the extrusion profile by controlling the material flow from at least one of the extruders. For example, one or more strips of material from one of the extruders can be eliminated by closing the appropriate cut off valves in the control lines coming from the extruder. The presence or absence of certain material strips will determine the stiffness of the finished extrusion profile as those skilled in the art will appreciate.

It is accordingly an object of the present invention to provide certain extrusion profiles such as catheters, for example, and a method for their manufacture.

It is another object of the present invention to provide an apparatus for the manufacture of certain extrusion profiles such as catheters and the like.

It is still another object of the present invention to provide extrusion profiles such as catheters as well as a method and apparatus for their manufacture wherein the catheters are manufactured from a plurality of strips of different materials to form a finished extrusion profile having varying physical properties along the longitudinal extent thereof.

These and other objects of the invention will be more apparent to those skilled in the art following a review of the remainder of the disclosure including the detailed description of the preferred embodiment and the appended claims.

BRIEF DESCRIPTION OF THE DRAWINGS

In describing the preferred embodiment of the invention, reference will be made to the attached drawings, in which.

DETAILED DESCRIPTION OF THE PREFERRED EMBODIMENT

Figure 1:
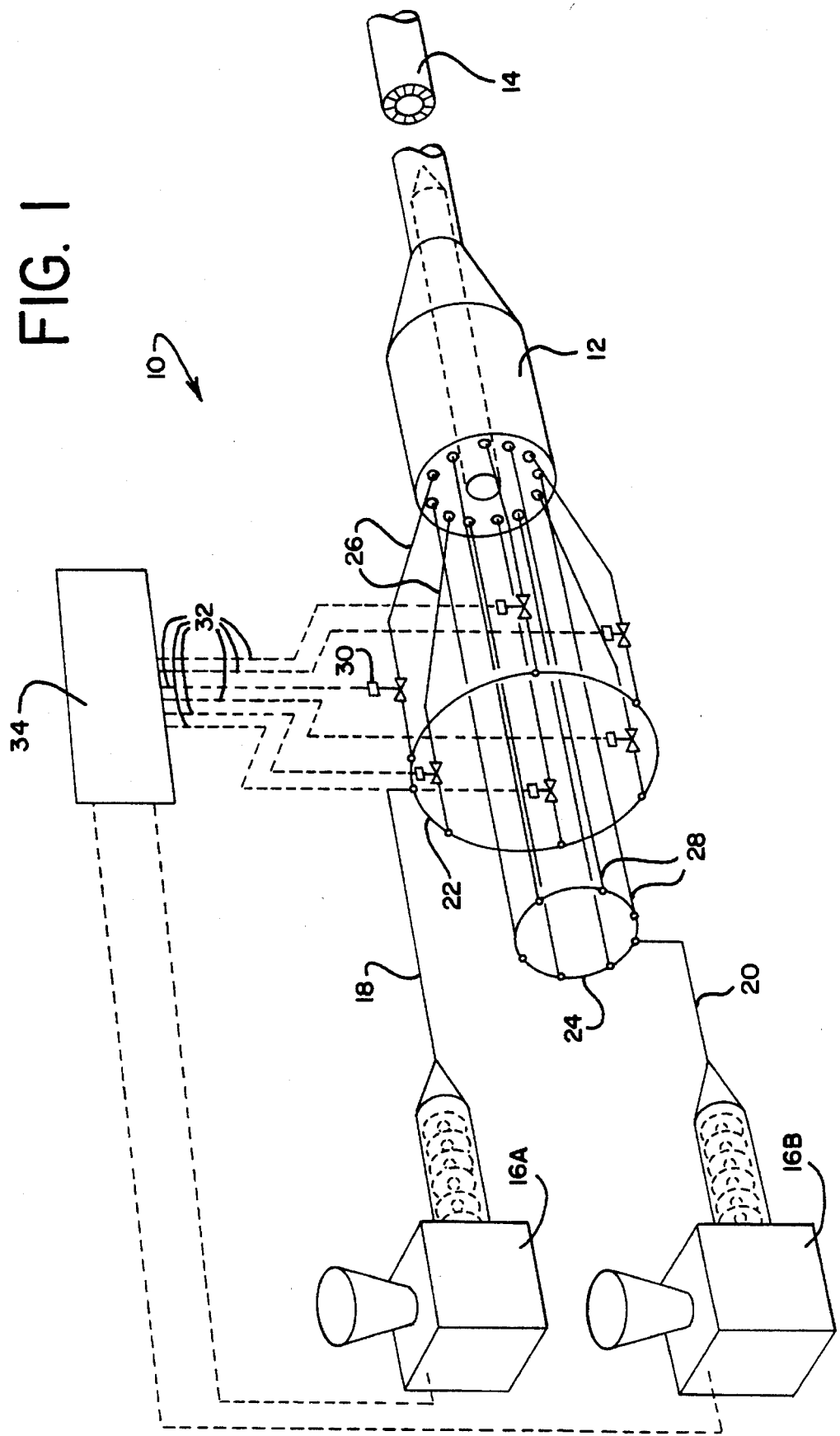
FIG. 1 illustrates schematically an apparatus and manufacturing method according to the invention.

Referring now to the Figures, FIG. 1 illustrates schematically an extrusion device for the manufacture of an extrusion profile according to the present invention. The apparatus 10 includes an extrusion nozzle 12 in which an extrusion profile such as the catheter 14 is formed. The method of the invention involves providing a plurality of material strips of at least two different compositions. The raw materials are each placed in an extruder 16 at the appropriate pressure and temperature to provide the correct degree of liquidity for the particular material being used. Material extruded from the first extruder 16A is conveyed through a line 18 to a distribution line 22. From the distribution line 22, branch lines 26 convey the stream of material to the extrusion nozzle 12.

The second extruder 16B sends molten material to line 20 which conveys the material to a distribution line 24. The distribution line 24 is, in turn, linked with a number of branch lines 28 conveying separate streams of material to the extrusion nozzle 12. As illustrated in FIG. 1, the apparatus 10 provides an extrusion profile 14 composed of twelve streams of material of two different compositions. The different materials can be incorporated in a pattern of alternating bands in the wall of the profile 14, as shown in FIG. 1. It is not intended, however, that the invention should be limited in any way to the use of twelve bands in the manufacture of extrusion profile 14. It is contemplated that extrusion profiles such as catheters and the like can be manufactured using more or less than twelve bands of material.

The branch lines 26 which convey a first material from the first extruder 16A, include along each line 26, cut off valves 30. A control means 34 is connected to the cut off valves 30 by control lines 32. The control means 34 can selectively open or close the valves 30 during the extrusion process in a controlled and known manner and thereby turn on and off the various streams of material conveyed through the corresponding branch lines 26. The control means 34 is preferably provided with means for controlling the two extruders 16A and 16B as well. Most preferably, the opening and closing of the cut off valves 30 is programmed in a preset cycle although manual operation of the valves 30 is also contemplated. As mentioned, the streams of material supplied by the extruders 16A and 16B are conveyed through the branch lines 26 and 28, respectively, and converge within the extrusion nozzle 12 to form the extrusion profile 14. After allowing the combined streams of materials to cool in a known manner, the extrusion profile 14 is available for further processing.

In the embodiment shown in FIG. 1, the streams of material provided by the second extruder 16B are conveyed continuously through the branch lines 28. The streams supplied by the first extruder 16A are conveyed through the branch lines 26 which can be opened and closed in a controlled manner by use of the cut off valves 30. For example, when the control means 34 closes all of the cut off valves 30, the extrusion profile 14 will be made entirely of the material conveyed from the second extruder 16B through the branch lines 28. When one of the cut off valves 30 is opened, the extrusion profile 14 would then include a single longitudinal strip of material coming from the first extruder 16A while the remainder of the profile 14 would, in cross-section, be made of material from the second extruder 16B.

Figure 2:
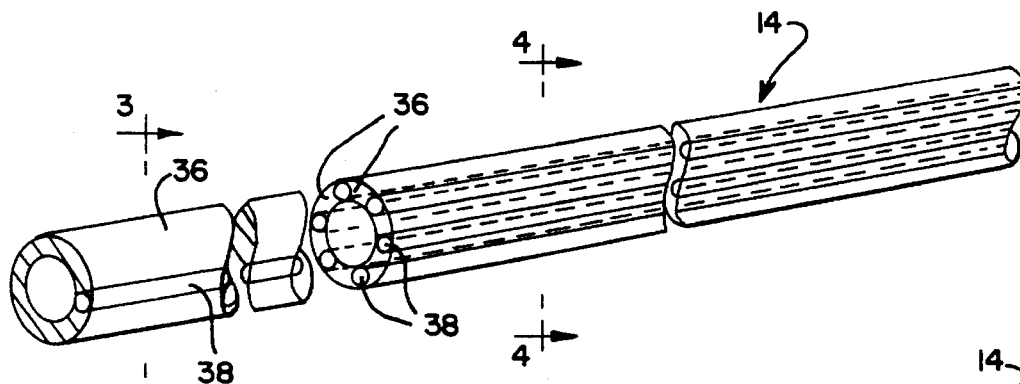
FIG. 2 illustrates an extrusion profile according to the present invention.
Figure 3:
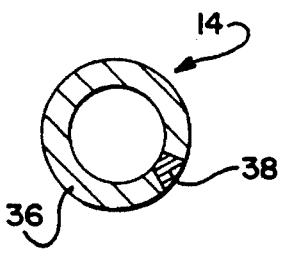
FIG. 3 shows the extrusion profile of FIG. 2 taken along the 3—3 line thereof.

The extrusion profile 14 illustrated in part in FIG. 2 and FIG. 3 represents, in cross-section, a section of a profile including only a single longitudinal band 38 supplied by the first extruder 16A. FIG. 3 represents a cross-section of the section of extrusion profile 14 taken along the 3—3 line of FIG. 2 and showing the single band 38 of material supplied by the first extruder 16A. The remainder of the cross-section consists of material 36 supplied by the second extruder 16B.

Figure 4:
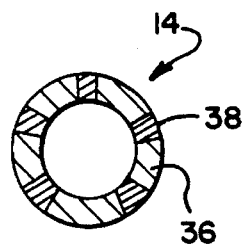
FIG. 4 shows a cross-section of the extrusion profile of FIG. 2 taken along the 4—4 line thereof.

FIG. 4 illustrates, in cross-section, an extrusion profile 14 taken along the 4—4 line of FIG. 2 illustrating a portion of a catheter or other extrusion profile resulting from the co-extrusion of materials through the extrusion nozzle 12 wherein all of the cut off valves 30 remained open during the manufacture of the illustrated portion of profile 14. The material 38 supplied by the first extruder 16A and the material 36 supplied by the second extruder 16B alternate in a regular fashion circumferentially. In this manner, the catheter or other extrusion profile 14 is manufactured with varying properties along its longitudinal axis corresponding to the properties of the constituent streams of material which are controlled by the opening and closing of the cut off valves 30.

For example, when the material supplied by the first extruder 16A is stiffer or harder than the material supplied by the second extruder 16B, the extrusion profile shown in cross-section in FIG. 3 will be less rigid than the section of the extrusion profile shown in cross-section in FIG. 4. By varying the number of cut off valves 30, as desired, the stiffness of the extrusion profile 14 can be altered gradually along the length of the profile 14. Either an abrupt or a more gradual transition of properties can be built into the finished extrusion profile 14 by controlling the flow of material from the first extruder 16A. A more gradual opening and closing of the cut off valves 11 will correspondingly create a more gradual transition of the physical properties of the finished extrusion profile. More abrupt changes in the physical properties of the profile 14 can be achieved by abruptly opening and closing the valves 30 during the extrusion process.

Figure 5:
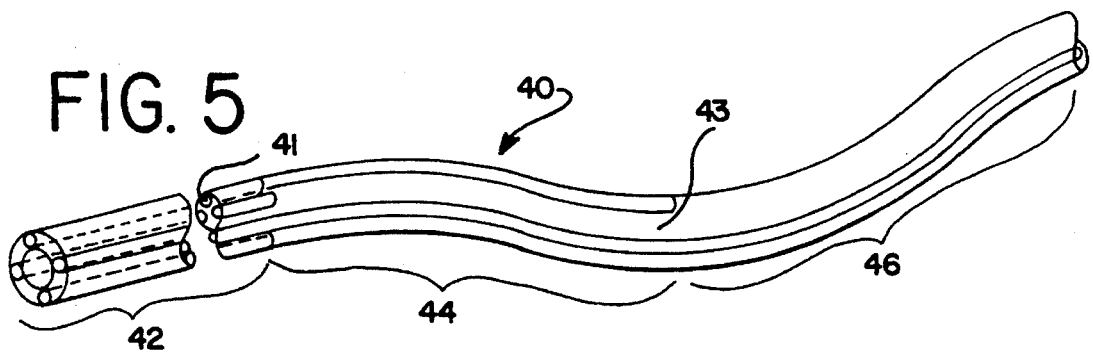
FIG. 5 shows another extrusion profile according to the present invention.

The extrusion profile 40 shown in FIG. 5 is representative of a catheter, for example, made of two different materials in accordance with the principles of the invention. The catheter 40 includes a first material 41 supplied by the first extruder 16A and a second material 43 supplied by the second extruder 16B. Within the first section 42 of the catheter 40, six bands of the first material 41 have been incorporated between six bands of the second material 43. Where the first material 41 is more rigid than the second material 43, for example, the first section 42 will be relatively rigid.

The second section 44 of the catheter 40 represents a transitional section containing two bands of the first material 41 while the remainder of the section 44 is made of the second material 43. Accordingly, the lowered amount of the first material 41 within the transitional section 44 will make the section 44 somewhat less rigid than the initial section 42 of the catheter 40. The transition from the first section 42 to the second section 40 is accomplished by closing at least four of the cut off valves 30 within the extrusion device 10 at the transition point from the first section 42 to the second section 44.

A third section 46 is also shown in FIG. 5 as including only one band of the first material 41. Hence the transition from the second section 44 to the third section 46 is accomplished by closing an additional cut off valve 30 within the extrusion device 10 to leave only one remaining stream of material being supplied by the first extruder to the extrusion profile or catheter 40 to thereby manufacture the third section 46. As a consequence of the reduced amount of the first material 41 within the third section 46, the section 46 is considerably less rigid and more pliable than the first section 42.

Figure 6:
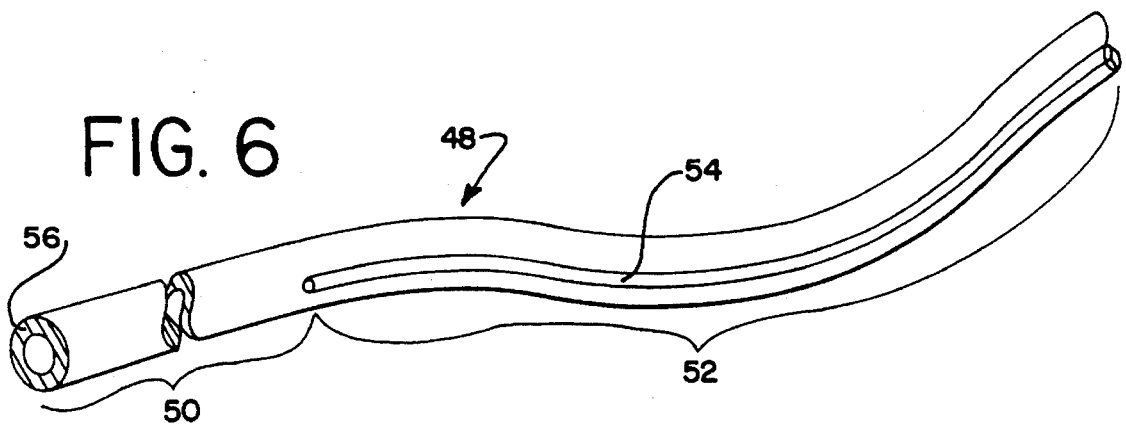
FIG. 6 shows yet another extrusion profile according to the present invention.

In addition to the rigidity or compliance of the finished product or extrusion profile, other properties can be incorporated therein. Referring now to FIG. 6, a catheter 48 is shown having two sections 50 and 52. The first section 50 of the catheter 48 is made of a single material 56 while the second section 52 includes a single band of a second material 54. The single band of a second material 54 within the second section 52 will alter the compliance properties of the catheter 48. It will be appreciated that the second material 54 can be one which will provide a high tensile stiffness such as a fiber bundle, for example. Accordingly, the section 52 of the catheter 48 can be made to bend in a particular preferential direction when a longitudinally compressive force is exerted on a portion of the section 52. Those skilled in the art will appreciate that the circumferential variance in stiffness due to the eccentric distribution of material strips along the section 54, will provide the catheter 48 with a certain steerability when the catheter is inserted within a vein or an artery of a living patient. In the section 52, for example, the segment will have a tendency to rotate toward the band or bands in the section of the catheter having less stiffness than the band 54. Where the band 54 is made of a material less stiff than the remainder of the section 52, the section will likewise exhibit a tendency to rotate toward band 54. Hence, a catheter, or segments thereof, can be made according to the invention to provide desired steerability properties.

Although the above description refers to streams of two different materials being supplied to manufacture an extrusion profile having a certain composition, the above description is not intended to be limiting in any way. It is contemplated, for example, that more than two different materials can be combined to form an extrusion profile. It is further contemplated that all of the streams of materials supplied to manufacture the finished extrusion profile can be turned on and/or off during the manufacturing process. For example, it is contemplated that an extrusion device such as the device 10 shown in FIG. 1, could be supplied with a second extruder 16B having cut off valves along the branch lines 28, for example. In this manner, materials supplied from the first and the second extruder 16A and 16B could both be controlled by the use of cut off valves to vary the number of streams of material being supplied to the extrusion nozzle 12. Additional extruders may also be placed within the manufacturing stream to manufacture an extrusion profile having three or more materials.

While a preferred embodiment of the present invention has been described in detail herein, it will be appreciated that changes and modifications can be made by those skilled in the art to the described embodiment without departing from the true spirit and scope of the invention as defined in the following claims.

I claim:

1. A tube-like extrusion profile having a proximal end and a distal end and suitable for use as a catheter and the like, comprising:

at least one strip of a first material extending longitudinally between a proximal portion and a distal portion of the tube-like extrusion profile to define a longitudinal length and to form at least part of a lumen and an outer surface of the profile;

at least one strip of a second material extending longitudinally between said proximal portion and said distal portion and forming another part of said lumen and said outer surface of said profile;

said first and said second material strips connected to each other in a side by side relationship along at least a portion of said profile to thereby form a generally tubular configuration, said first material being different from said second material such that the physical characteristics of said extrusion profile are determined in part by the respective relative amounts of said first and said second materials within said profile; and said relative amount of said first material varies along said longitudinal length.

2. The tube-like extrusion profile as defined in claim 1 wherein at least a portion of said extrusion profile, in transverse cross section, is composed of an equal number of said first and said second material strips, and said first and said second strips are arranged within said cross section in an alternating pattern.

3. The tube-like extrusion profile as defined in claim 1 wherein at least a portion of said extrusion profile, in transverse cross section, contains a greater number of said strips of second material than of said strips of first material.

4. The tube-like extrusion profile as defined in claim 1 wherein said strip of first material includes fiber bundles.

5. The tube-like extrusion profile as defined in claim 1 wherein said relative amount of said second material varies along said longitudinal length.

6. The tube-like extrusion profile as defined in claim 1 wherein said longitudinal length has at least one section which has its wall consist of longitudinal bands manufactured of said first and second different materials.

7. The tube-like extrusion profile as defined in claim 6 wherein the cross-section of at least two of said longitudinal bands varies along said longitudinal length.

8. The tube-like extrusion profile as defined in claim 7 wherein said first material is more rigid than said second material, and wherein the total transverse cross-sectional area of said first material is less in said distal portion than in said proximal portion.

9. The tube-like extrusion profile as defined in claim 1 wherein said relative amount that the first material varies is determined during coextrusion of said first and second materials during which an extruded stream of said first material is turned on and off in a controlled manner.

10. The tube-like extrusion profile as defined in claim 5 wherein said relative amount that the second material varies is determined during coextrusion of said first and second materials during which an extruded stream of said second material is turned on and off in a controlled manner.

\* \* \* \* \*

UNITED STATES PATENT AND TRADEMARK OFFICE
CERTIFICATE OF CORRECTION

PATENT NO. : 5,456,674
DATED : October 10, 1995
INVENTOR(S) : Johannes Bos, Frans Mous and Johannes G.M. van Muiden It is certified that error appears in the above-indentified patent and that said Letters Patent is hereby corrected as shown below:

On the Cover Page, under "Attorney, Agent, or Firm", replace "Fritzgibbon" with --FitzGibbon--.
Col. 1, line 9, "properties long" should read --properties along--; line 36, "cross sectional" should read --cross-sectional--.
Col. 2, lines 5-6, "cross sections" should read --cross-sections--; line 7, "cross section" should read --cross-section--; line 10, delete "catheter".
Col. 6, line 28, "cross section" should read --cross-section--; line 30, "cross section" should read --cross-section--; line 34, "cross section" should read --cross-section--.

Signed and Sealed this

Twentieth Day of August, 1996

Attest:

BRUCE LEHMAN

Attesting Officer

Commissioner of Patents and Trademarks